United States Patent [19]

Auld

[11] 4,364,012
[45] Dec. 14, 1982

[54] FMR PROBE METHOD UTILIZING MAIN AND SPURIOUS RESONANCE MODES FOR DETECTING SURFACE FLAWS

[75] Inventor: Bertram A. Auld, Menlo Park, Calif.

[73] Assignee: The Board of Trustees of the Leland Stanford Junior University, Palo Alto, Calif.

[21] Appl. No.: 126,196

[22] Filed: Mar. 3, 1980

[51] Int. Cl.³ .................... G01R 33/12; G01N 27/82; G01N 22/02
[52] U.S. Cl. ........................................ 324/237; 331/96
[58] Field of Search ................ 324/233, 225, 236–238, 324/250, 58 R, 58 B, 58 C, 58.5 R, 58.5 B, 58.5 C, 301, 307, 319; 331/96, 107 DP, 65

[56] References Cited

U.S. PATENT DOCUMENTS

| 2,799,823 | 7/1957 | Shaw et al. | 324/307 |
| 2,832,040 | 4/1958 | Harmon | 324/237 |
| 2,948,845 | 8/1960 | Handel | 324/319 |
| 3,085,196 | 4/1963 | Martin | 324/301 |
| 3,159,784 | 12/1964 | Haslett et al. | 324/238 X |
| 3,302,105 | 1/1967 | Libby et al. | 324/233 |
| 3,576,503 | 4/1971 | Hanson | 331/96 |
| 3,909,746 | 9/1975 | Abraham et al. | 331/107 DP X |
| 3,931,571 | 1/1976 | Hocking et al. | 324/236 |
| 4,048,588 | 9/1977 | Zublin et al. | 331/96 |
| 4,155,035 | 5/1979 | Fitzky | 324/58.5 C |
| 4,290,017 | 9/1981 | Fortunko | 324/237 |

FOREIGN PATENT DOCUMENTS 55-43420  3/1980  Japan .................................... 324/238

Primary Examiner—Gerard R. Strecker
Attorney, Agent, or Firm—Flehr, Hohbach, Test, Albritton & Herbert

[57] ABSTRACT

In ferromagnetic resonance (FMR) probe apparatus for detecting surface flaws in a metal surface, probe impedance changes resulting from flaws are distinguished from impedance changes resulting from probe lift-off from the metal surface. A constant magnitude dc magnetic field and a constant frequency and constant magnitude rf magnetic field are applied to the ferromagnetic crystal and the real and imaginary components of probe impedance are detected. The impedance changes due to flaws are at least partially orthogonal to the impedance changes due to lift-out, and by observing probe impedance on an oscilloscope the presence of a flow or the occurrence of lift-off are readily identified.

3 Claims, 7 Drawing Figures

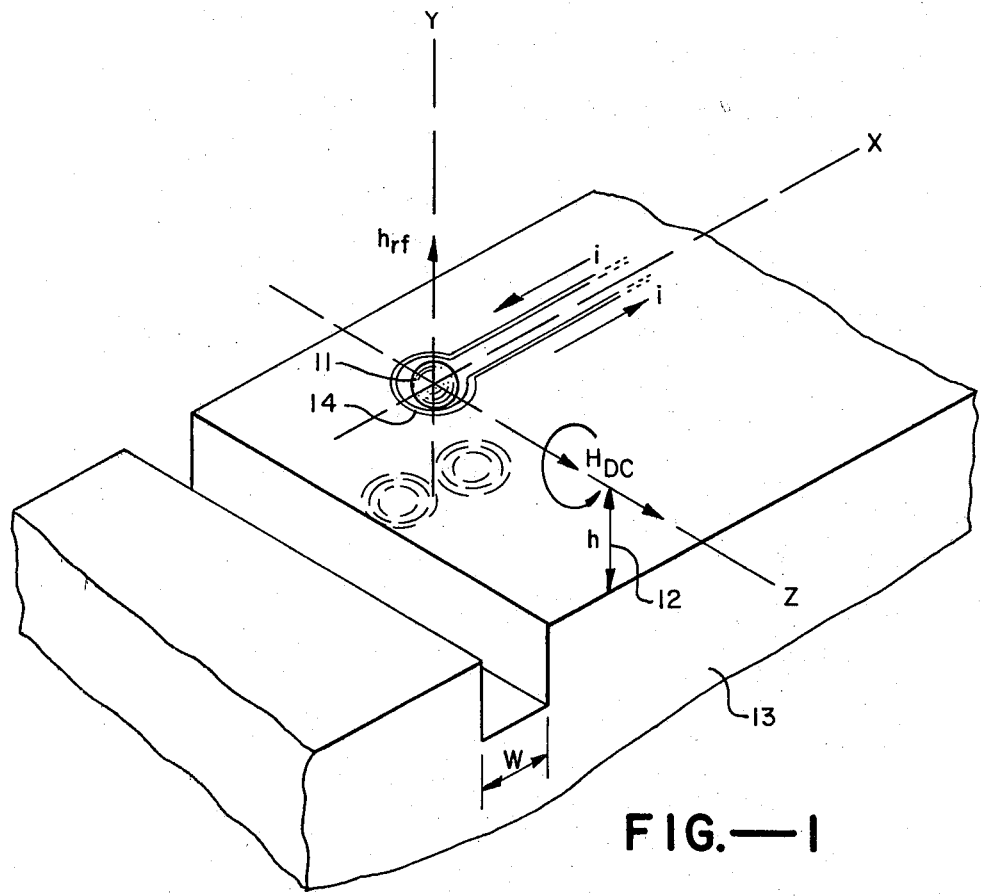
FIG.—1
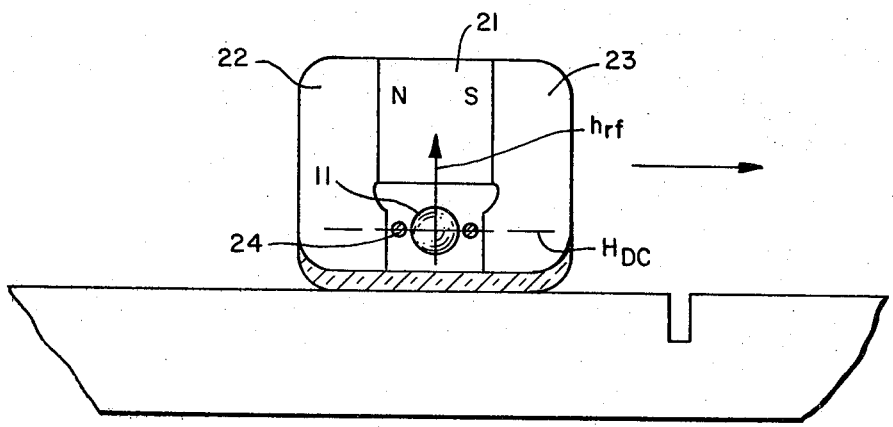
FIG.—2

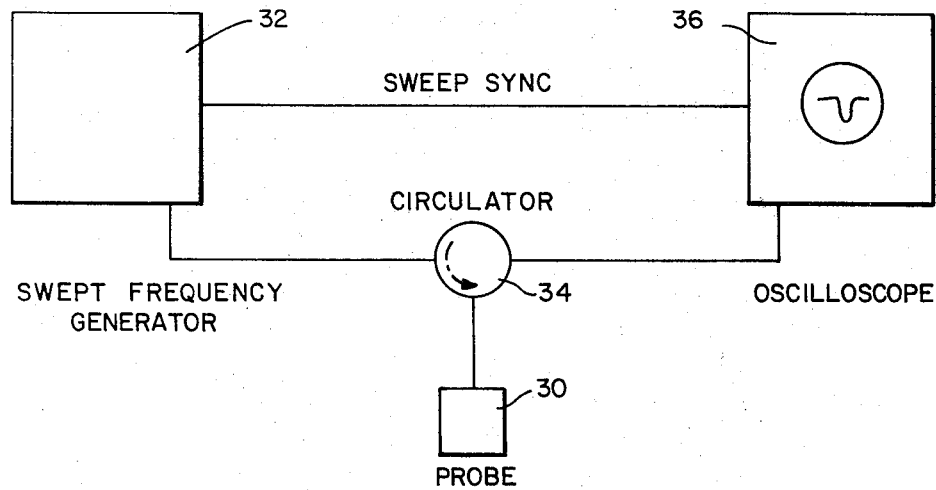
FIG.—3
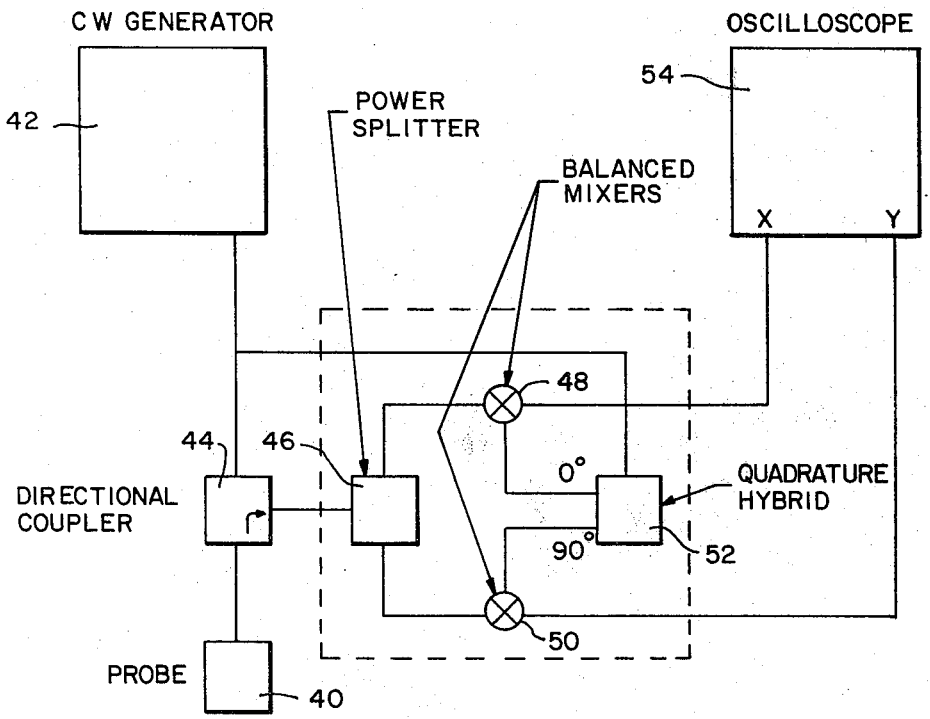
FIG.—4

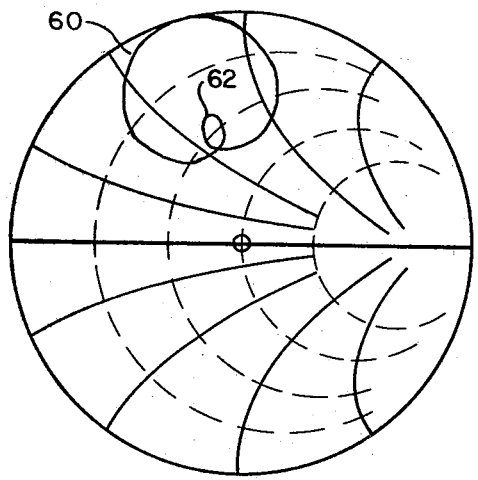
FIG.—5
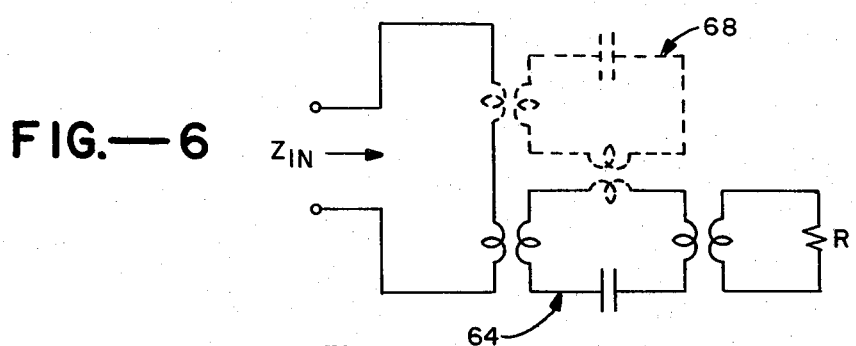
FIG.—6
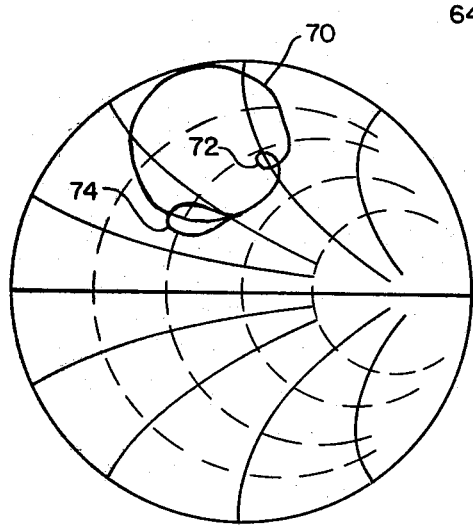
FIG.—7

FMR PROBE METHOD UTILIZING MAIN AND SPURIOUS RESONANCE MODES FOR DETECTING SURFACE FLAWS

This invention relates generally to ferromagnetic resonance (FMR) probes and methods for inspecting a surface for flaws.

A ferromagnetic resonance probe and a method of detecting surface flaws in metals are disclosed in co-pending application Ser. No. 961,046 filed Nov. 15, 1978, now U.S. Pat. No. 4,286,216. The ferromagnetic resonator is a small sphere of ferro-magnetic crystal placed in a dc magnetic field and excited by a microwave frequency current flowing in a wire loop encircling the sphere. The resonance phenomenon is a precessional motion of the crystal's inherent magnetic moment about the direction of the dc magnetic field. This precessing magnetic moment induces surface currents in the magnetic test sample, and the disturbance of these currents by a surface flaw produces a detectable flaw signal at the electrical terminals of the wire loop.

In detecting flaws in a metal surface using the ferromagnetic resonance probe, the probe is moved with respect to the surface of the metal and changes in the probe impedance are detected. The probe is excited by a microwave generator which produces a voltage whose frequency is swept linearly with time. An oscilloscope display of the probe reflection coefficient as a function of frequency permits observation of the resonance dip and its frequency shift produced by scanning over a flaw. A difficulty with the disclosed method is that lift-off variations between the probe and the metal surface also produced a frequency shift. Thus, a method and means is required to differentiate between a surface flaw and a lift-off variation.

Accordingly, an object of the present invention is a ferro-magnetic resonance probe apparatus which distinguishes between a surface flaw and lift-off variations.

Another object of the invention is a method of operating a ferromagnetic resonance probe whereby lift-off variations can be distinguished from variations due to surface defects.

In accordance with the invention, apparatus for detecting flaws in a metal surface includes a probe including a ferro-magnetic resonator, means for applying a dc bias magnetic field to the resonator, means for receiving an rf signal and applying an rf magnetic field to said resonator with a component of the rf field being orthogonal to said dc magnetic field, and means for determining the impedance of said probe as measured at the input terminal. Field coupling in the probe is adjusted whereby a main resonance mode and at least one spurious mode of resonance are present. More particularly, the means for measuring input impedance determines both the real and imaginary components thereof and may comprise a polar phase discriminator. The polar phase discriminator may include a cathode ray tube on which the real and imaginary components of the input impedance are projected.

In detecting flaws in a metal surface with the apparatus in accordance with the invention, the ferromagnetic resonator is placed adjacent to the surface to be examined. The dc magnetic field and rf magnetic field are applied to the ferromagnetic resonator, and the probe is then scanned across the surface being examined. Changes in input impedance of the probe are detected while the probe is scanned, thereby identifying the presence of surface flaws by changes in input impedance. Advantageously, changes in input impedance resulting from lift-off of the probe from the surface being examined can be more readily discriminated from impedance changes due to surface flaws by providing a plurality of resonance modes in the probe.

The invention and objects and features thereof will be more readily apparent from the following detailed description and appended claims when taken with the drawings, in which:

FIG. 1 is a schematic illustration of a ferromagnetic probe.

FIG. 2 is a front view of the probe of FIG. 1.

FIG. 3 is a functional block diagram illustrating the operation of the probe of FIGS. 1 and 2.

FIG. 4 is a functional block diagram of a probe and circuitry in accordance with one embodiment of the present invention.

FIG. 5 is a Smith chart representation of the impedance of a probe in accordance with the invention.

FIG. 6 is an equivalent circuit of a probe in accordance with the invention.

FIG. 7 is a Smith chart representation of the impedance of a probe in accordance with the invention responsive to lift-off.

Referring now to the drawings, FIG. 1 illustrates a microwave flaw testing probe as disclosed in co-pending application Ser. No. 961,046. The probe includes a resonator which may take the form of an yttrium iron garnet (YIG) sphere with a volume of less than $10^{-4}$ cubic inch and a resonance $Q = 1,000$. The dc magnetic field bias, $H_{DC}$, required for ferromagnetic resonances can be supplied by small permanent magnets which can be part of the probe. Microwave excitation of the resonator is provided by a small coupling loop placed near the resonator and electromagnetically coupled thereto.

As illustrated, the resonator 11 is placed at a height or distance h from the surface 12 of the metal 13 to be tested. A coupling loop 14 provides high frequency field $H_{rf}$ to the resonator by means of rf current, i, flowing through the loop. A dc magnetic field H is provided which may be orthogonal to the magnetic field $h_{rf}$. Precession of the spins in the YIG material about the dc field, H, occurs because of the dc and rf magnetic fields. The precession is resonant about the dc bias field at a frequency which is determined by the magnitude of the dc field, H, and the rf dc magnetizing fields arising from the magnetic poles produced at the boundaries.

Referring to FIG. 2, there is schematically shown a probe as illustrated in FIG. 1. The probe includes a resonator 11. A magnet 21 provides dc magnetic field H to pole pieces 22 and 23. A coil 24 provides the orthogonal rf magnetic field $H_{rf}$. A thin plastic cover 26 provides a mechanical means for maintaining a uniform height, H, above the surface. Thus, in use, the probe can be brought into contact with a surface and moved therealong.

FIG. 3 is a functional block diagram illustrating the operation of the probe illustrated in FIGS. 1 and 2 and as described in co-pending application Ser. No. 961,046. As the probe 30 is moved across the surface of the metal under examination, sweep generator 32 provides a linearly swept frequency signal to the probe through circulator 34, and the frequency response of probe 30 to the swept frequency is displayed on oscilloscope 36. The oscilloscope display of the probe's reflection coefficient as a function of frequency permits observation of a resonance dip and frequency shift due to the presence of a surface flaw. Unfortunately, lift-off of the probe from the surface being scanned also produces a frequency shift which is not readily distinguished from the flaw frequency shift using the apparatus and method of co-pending application Ser. No. 961,046.

In accordance with the present invention the frequency applied to the probe is maintained constant and the real and imaginary components of the probe impedance are measured to determine the presence of frequency shift due to a flaw as opposed to an impedance change due to probe lift-off from the surface under examination. FIG. 4 illustrates apparatus in accordance with one embodiment for carrying out the invention. The apparatus employs a polar phase discriminator (standard microwave circuitry) to monitor and display the complex input impedance of the probe 40. A fixed frequency signal from microwave generator 42 is applied to the probe through directional coupler 44 as the probe is scanned across the surface under examination. The voltage reflected from the probe 40 is applied through directional coupler 44 to a phase splitter 46 which applies the reflected signal from probe 40 to balance mixers 48 and 50 which mix the reflected signal with phase quadrature signals from hybrid 52. The outputs of mixers 48, 50 are then applied to an oscilloscope 54 as the X and Y input signals. The fixed frequency signal may be in the range of 500–4,000 MHz, and the signal from hybrid 52 is at the same frequency, thereby giving output signals to the oscilloscope at dc or low frequencies (e.g. up to about 60 Hz).

Oscilloscope 54 presents on the X and Y axes the real and imaginary parts of the complex reflection coefficient, $\Gamma$ at the probe terminals. This quantity is related to impedance by the formula $$(Z/Z_0) = (1+\Gamma)/1-\Gamma)$$

where $Z_0$ is a characteristic impedance in the electrical transmission line feeding the probe. Since the oscilloscope display is a polar representation, the oscilloscope display is in the form of a Smith chart as illustrated in FIG. 5, where the dashed lines represent constant resistance (or real part of impedance) and the solid lines represent constant reactance (or imaginary part of impedance).

FIG. 5 is a Smith chart representation of probe impedance as a function of frequency, and it will be noted that the main resonance circle 60 includes a secondary circle 62 which is due to coupling of a spurious magnetostatic mode of the ferromagnetic resonance probe. Such a spurious mode can be introduced by suitably adjusting the position and direction of the permanent magnet and dc field, H, in the probe of FIG. 2. The coupling of the spurious mode causes a surface flaw response curve in the complex impedance plane that is more readily discriminated from the lift-off curve. The equivalent circuit of the probe including a spurious mode is illustrated in FIG. 6 where the input impedance $Z_{in}$ across the input terminals to the probe is determined by magnetic coupling to a main resonant circuit shown generally at 66 and the spur resonant circuit shown in dotted form at 68.

By so coupling a spurious mode in the probe, a flaw response curve in the complex impedance plane is caused to be more orthogonal to the lift-off curve. This is illustrated in FIG. 7 which is a Smith chart display of probe impedance variations at constant frequency where the impedance changes due to lift-off are represented by the circular response 70 including the smaller circle 72 due to spurious response, while the impedance variation due to the surface flaw is generally tear shaped in configuration as illustrated at 74. The lift-off curve of the probe arises from the detuning of the excited resonator and follows the resonance curve 70 and 72. While improved lift-off discrimination appears to require coupling to some spurious mode, the coupling need not be strong as good lift-off discrimination has been achieved with a probe frequency response curve that is almost a perfect circle, with only a small dimple or flattening to indicate the presence of a second, spurious mode.

Thus, a probe capable of improved discriminating between variations in frequency response resulting from the presence of a flaw and resulting from the lift-off of the probe from the surface under examination has been described. By exciting a spurious mode in the probe, the input impedance at a fixed frequency of the probe shows an increased difference between the presence of a surface flaw and of probe lift-off.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. The method of detecting and distinguishing flaws in a metal surface detected by means of a ferromagnetic resonance probe from signals generated due to probe lift-off from the metal surface comprising the steps of:
    placing a ferromagnetic resonator adjacent to the surface, said resonator having a plurality of resonance modes,
    applying a dc magnetic field to said resonator,
    applying an rf magnetic field to said resonator,
    field coupling said probe and said surface with a main resonance mode and simultaneously at least one spurious mode of resonance,
    scanning said probe across said surface during said field coupling, and
    detecting during said scanning real and imaginary changes in impedance of said probe at a fixed frequency whereby probe impedance variation due to a flaw is generally orthogonal to probe impedance variation due to probe lift-off from said surface.

2. The method of detecting flaws in a metal surface as defined by claim 1 wherein said step of detecting changes in impedance includes displaying real and imaginary components of impedance on a cathode ray tube.

3. The method of detecting flaws as defined by claim 1 or 2 wherein said step of applying a dc magnetic field includes maintaining the dc magnetic field constant in magnitude, and said step of applying an rf magnetic field includes maintaining said rf magnetic field constant in frequency and magnitude.

* * * * *